United States Patent
Li et al.

(10) Patent No.: US 10,131,643 B2
(45) Date of Patent: Nov. 20, 2018

(54) TIZOXANIDE CARBAMATE AND PHARMACEUTICAL USE THEREOF

(71) Applicant: Institute of Pharmacology and Toxicology Academy of Military Medical Sciences P.L.A. China, Beijing (CN)

(72) Inventors: Song Li, Beijing (CN); Xingzhou Li, Beijing (CN); Wu Zhong, Beijing (CN); Zhibing Zheng, Beijing (CN); Junhai Xiao, Beijing (CN); Xinbo Zhou, Beijing (CN); Yunde Xie, Beijing (CN); Xiaokui Wang, Beijing (CN); Lili Wang, Beijing (CN); Wei Chen, Beijing (CN); Fei Xie, Beijing (CN)

(73) Assignee: Institute of Pharmacology and Toxicology Academy of Military Medical Sciences P.L.A. China, Haidian District, Beijing (CN)

( * ) Notice: Subject to any disclaimer, the term of this patent is extended or adjusted under 35 U.S.C. 154(b) by 0 days.

(21) Appl. No.: 14/901,805

(22) PCT Filed: Jul. 4, 2014

(86) PCT No.: PCT/CN2014/081626
§ 371 (c)(1),
(2) Date: Dec. 29, 2015

(87) PCT Pub. No.: WO2015/000431
PCT Pub. Date: Jan. 8, 2015

(65) Prior Publication Data
US 2016/0340326 A1    Nov. 24, 2016

(30) Foreign Application Priority Data

Jul. 4, 2013 (CN) .......................... 2013 1 0277710

(51) Int. Cl.
*C07D 277/58* (2006.01)
*C07D 401/12* (2006.01)
*C07D 417/12* (2006.01)

(52) U.S. Cl.
CPC ......... *C07D 277/58* (2013.01); *C07D 401/12* (2013.01); *C07D 417/12* (2013.01)

(58) Field of Classification Search
CPC ... C07D 277/58; C07D 401/12; C07D 417/12
See application file for complete search history.

(56) References Cited

U.S. PATENT DOCUMENTS

| | | | |
|---|---|---|---|
| 8,772,502 B2 | 7/2014 | Semple et al. | |
| 9,023,877 B2 | 5/2015 | Rossignol et al. | |
| 2010/0330173 A1 | 12/2010 | Rossignol et al. | |
| 2012/0108591 A1 | 5/2012 | Semple et al. | |

FOREIGN PATENT DOCUMENTS

| | | |
|---|---|---|
| CN | 102480967 A | 5/2012 |
| CN | 103269593 A | 8/2013 |
| WO | WO 2010/101648 A1 | 9/2010 |
| WO | WO 2010/151577 A1 | 12/2010 |
| WO | WO 2012/061190 A1 | 5/2012 |

OTHER PUBLICATIONS

International Search Report (ISR) for PCT/CN2014/081626; I.A. fd: Jul. 4, 2014, dated Oct. 26, 2015, State Intellectual Property Office of the P.R. China, Beijing, China.
International Preliminary Report on Patentability (IPRP) including the Written Opinion of the International Searching Authority (PCT Rule 44bis) for PCT/CN2014/081626; I.A. fd: Jul. 4, 2014, dated Jan. 5, 2016, and Jan. 19, 2016 (the translation) by the International Bureau of WIPO, Geneva, Switzerland.
Li, Shao-hua et al., "The improved preparation of nitazoxanide," Chinese J Modern Appl. Pharmacy (JMAP) 23(5) 368-369; (Oct. 2006), Hangzhou:Zhongguo xian dai ying yong yao xue bian ji wei yuan hui, publisher; China.
Qiang, Xiaoming, "Synthesis and biological evaluation of genistein carbamate derivatives," Chinese J Organic Chem 33:621-629 (2013); published online Nov. 23, 2012; Chinese Chemical Society & SIOC, China.
Extended European search report, including the supplemental European search report and the European search opinion, for EP Appl. No. 14820360.7, dated Oct. 6, 2016, European Patent Office, Munich, Germany.
Rautio, J et al.,"Prodrugs: design and clinical applications," Nat Rev Drug Discov. Mar. 2008;7(3):255-70. doi: 10.1038/nrd2468.

*Primary Examiner* — Kendra D Carter
(74) *Attorney, Agent, or Firm* — Sterne, Kessler, Goldstein & Fox P.L.L.C.

(57) ABSTRACT

The invention relates to a tizoxanide carbamate compound of Formula I and a pharmaceutically acceptable salt, a hydrate or a solvate thereof, and their pharmaceutical use.

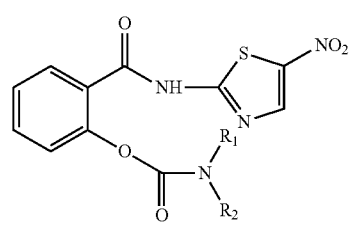

12 Claims, 1 Drawing Sheet

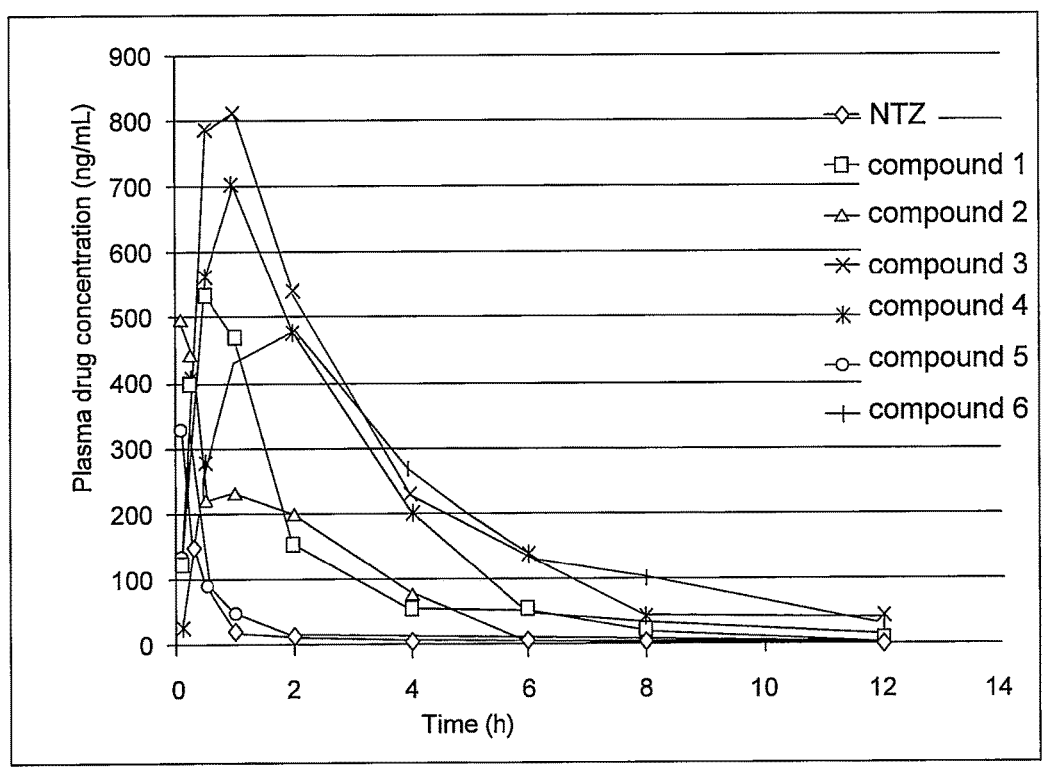

TIZOXANIDE CARBAMATE AND PHARMACEUTICAL USE THEREOF

TECHNICAL FIELD

The invention relates to tizoxanide aminocarboxylate compounds, particularly a class of tizoxanide carbamate compounds and pharmaceutically acceptable salts, hydrates or solvates thereof, and pharmaceutical uses thereof.

BACKGROUND ART

Nitazoxanide (NTZ), which is a thiazolyl benzamide compound developed by Romark Laboratory, has multiple bioactivities. NTZ has a chemical name of "2-acetoxy-N-(5-nitro-2-thiazolyl)benzamide", a chemical formula of $C_{12}H_9N_3O_5S$, and a melting point of 202° C., and is a light yellow powder, which is insoluble in water, slightly soluble in ethanol, and soluble in organic solvents such as tetrahydrofuran, dimethyl sulfoxide (DMSO) and N,N-dimethylformamide (DMF). Studies have shown that nitazoxanide is effective in combating a variety of parasites in human such as protozoan, helminth, specifically including: *Giardia, Amoeba, Cryptosporidium, Cyclospora, Trichomonad, Encephalitozoon intestinalis, Isospora belli, Blastocystis hominis, Balantidium coli, Ascaris lumbricoides, Enteracytozoon bieneusi, Tapeworm* (including *Taenia saginata, Hymenolepis nana*), *Diplacanthus nanus, Giardia lamblia, Leishmania, Fasciola hepatica*, etc. Nitazoxanide has good therapeutic effect on viral infectious diseases such as hepatitis B (HBV), hepatitis C (HCV), influenza (including canine influenza), and viral enterogastritis caused by Rotavirus or Norovirus. Nitazoxanide is also useful in combating infection caused by bacteria such as *Clostridium difficile* (CD), *Tubercle bacillus* (including drug-resistant *Tubercle bacillus*) and *Helicobacter pylori*, and also has a good inhibitory effect on the biofilm formation caused by bacteria.

Nitazoxanide is a prodrug which is quickly hydrolyzed to its active metabolite tizoxanide (TIZ) in vivo after administration. The pharmacokinetic studies in human show that after oral administration, nitazoxanide is absorbed by gastrointestinal tract, wherein about ⅓ of the oral dose is excreted by urine, and about ⅔ of the oral dose is excreted by feces. In blood, nitazoxanide is quickly metabolized by plasma esterase (the half life is about 6 mill at 37° C.), and is deacetylated by hydrolysis to produce its active metabolite tizoxanide. Therefore, nitazoxanide is not detectable in plasma, urine, bile and feces. Tizoxanide can be further subjected to glucuronidation in vivo to produce tizoxanide glucuronide having no pharmaceutical activity. Tizoxanide is present in plasma, urine, bile and feces, and tizoxanide glucuronide is also present in plasma, urine and bile.

Nitazoxanide has good pharmaceutical properties such as multiple bioactivities and good safety, but also has some obvious disadvantages, which mainly reside in the following two aspects.

(1) Nitazoxanide has the shortcomings such as low bioavailability, short half life, and low blood concentration. It is found by Pharmacokinetic Laboratory of Institute of pharmacology & Toxicology Academy of Military Medical Sciences that when nitazoxanide suspension was orally administered to rats, the absolute bioavailability was only 7.2%. In addition, it is reported in papers that when nitazoxanide was orally administered to healthy adults, after single administration of 500 mg, the active metabolite tizoxanide had a time to peak ($T_{max}$) of 3-4 h, a AUC value of about 3.9-11.3 μg*h/mL, a maximum concentration ($C_{max}$) of 1.9 μg/mL (in the range of 1.1-2.5), and a short half life of only from 1.03 to 1.6 h.

(2) Nitazoxanide has relatively low activity, for example, nitazoxanide has a minimal inhibitory concentration (MIC) of from 12 to 28 μg/ml, (the median value is 16 μg/mL) for *Mycobacterium tuberculosis*; nitazoxanide and tizoxanide have the minimal inhibitory concentrations (MICs) of between 0.25 and 8 μg/mL, the 50% minimal inhibitory concentration ($MIC_{50}$) of 1 μg/mL, and the 90% minimal inhibitory concentration ($MIC_{90}$) of 4 μg/mL, for 103 strains of *Helicobacter pylori*; under aerobic or microaerophilic conditions, nitazoxanide and tizoxanide have a minimal inhibitory concentration (MIC) of 8~16 μg/mL for *Staphylococcus epidermidis* or other *Staphylococcus* (including methicillin resistant *Staphylococcus aureus*); nitazoxanide has an $EC_{50}$ of 1 μg/mL and an $EC_{90}$ of 7 μg/mL for PR8 influenza virus in MDCK cells.

As can be seen, nitazoxanide has the shortcomings of low bioavailability, short half life, and low blood concentration. When nitazoxanide is used in the treatment of infections by parasites such as intestinal protozoans and helminths, nitazoxanide can work without entering blood. Therefore, the properties of nitazoxanide, i.e., poor oral absorption, low bioavailability, and low blood concentration, would not influence its therapeutic effect on the treatment of infections by parasites such as intestinal protozoans and helminths. However, if nitazoxanide is applied to the treatment of drug-resistant *Tubercle bacillus, Helicobacter pylori* or methicillin resistant *Staphylococcus aureus*, or the treatment of viral infectious diseases caused by influenza virus, Rotavirus and the like, the blood concentration should be higher than or close to the 90% minimal inhibitory concentration ($MIC_{90}$) or to the effective concentration for 90% inhibition of virus ($EC_{90}$). The shortcomings of nitazoxanide, i.e., poor oral absorption, low bioavailability, and low blood concentration, are necessarily observed and directly influence its pharmaceutical effect.

Therefore, if nitazoxanide agent is applied to the treatment of drug-resistant *tubercle bacillus, Helicobacter pylori* or methicillin resistant *Staphylococcus aureus*, or the treatment of viral infectious diseases caused by influenza virus, Rotavirus and the like, it will be necessary to enhance the bioavailability, increase the blood concentration, and prolong the half life of nitazoxanide calculated as tizoxanide, so as to have therapeutic effects such as anti-bacterial and anti-viral effects.

CONTENTS OF INVENTION

The inventor of the invention surprisingly found that when tizoxanide as a parent compound is modified to a carbamate compound, for the compound calculated as tizoxanide, its bioavailability is effectively improved, its blood concentration is increased, and its half life is prolonged, and therefore the therapeutic effects of nitazoxanide agents, such as anti-bacterial and anti-viral effects, are improved.

The invention provides a series of tizoxanide carbamate compounds, which can be converted into the form of tizoxanide in vivo so as to exert an action against protozoans, helminths, viruses or bacteria, wherein for these compounds calculated as nitazoxanide, the bioavailability and the blood concentration are improved significantly, the effective blood concentration is retained for a longer time, and the blood concentration curve is more stable.

In the first aspect, the invention relates to a tizoxanide carbamate compound represented by Formula I,

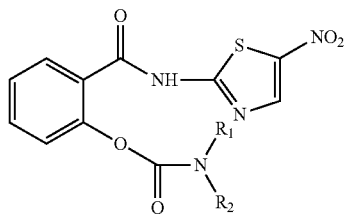

or a pharmaceutically acceptable salt, a hydrate or a solvate thereof, wherein: $R_1$ and $R_2$ each are independently selected from a group consisting of hydrogen, and $C_{1-4}$ alkyl; or $R_1$ is linked to $R_2$, and $R_1$, $R_2$ together with the adjacent N atom, form a 4-8 membered N-containing heterocycle; or $R_1$ is linked to $R_2$, and $R_1$, $R_2$ together with the adjacent N atom, form a O-containing and/or N-containing 3-10 membered heterocycle; the 4-8 membered N-containing heterocycle or the O-containing and/or N-containing 3-10 membered heterocycle is optionally substituted with one or more (e.g., 1-5, 1-4, 1-3, or 1-2) substituents independently selected from a group consisting of: halogen (e.g., F, Cl, Br, I), hydroxyl, $C_{1-4}$ alkyl, $C_{1-4}$ alkoxyl, $C_{1-4}$ alkoxycarbonyl, carboxyl, nitro, amino, and carbonyl.

In a preferred embodiment, provided is the compound of Formula I according to the first aspect of the invention, wherein $R_1$ and $R_2$ each are independently selected from a group consisting of hydrogen, methyl, ethyl, n-propyl, isopropyl, n-butyl, sec-butyl, and tert-butyl; or $R_1$ is linked to $R_2$, and $R_1$, $R_2$ together with the adjacent N atom, form a 5-membered N-containing heterocycle or 6-membered N-containing heterocycle; or $R_1$ is linked to $R_2$, and $R_1$, $R_2$ together with the adjacent N atom, form a O-containing and/or N-containing 6-membered heterocycle; the 5-membered N-containing heterocycle or 6-membered N-containing heterocycle, or the O-containing and/or N-containing 6-membered heterocycle is optionally substituted with one or more (e.g., 1-5, 1-4, 1-3, or 1-2) substituents independently selected from a group consisting of: halogen (e.g., F, Cl, Br, I), hydroxyl, $C_{1-4}$ alkyl, $C_{1-4}$ alkoxyl, $C_{1-4}$ alkoxycarbonyl, carboxyl, nitro, amino, and carbonyl.

In another preferred embodiment, provided is the compound of Formula I according to the first aspect of the invention, wherein $R_1$ and $R_2$ are each are independently selected from a group consisting of hydrogen, methyl, ethyl, n-propyl and isopropyl; or $R_1$ is linked to $R_2$, and $R_1$, $R_2$ together with the adjacent N atom, form 5-membered or 6-membered heterocycle, the 5-membered or 6-membered heterocycle includes: piperazine, morpholine, piperidine or pyrrolidine; the 5-membered or 6-membered heterocycle is optionally substituted with a substituent selected from a group consisting of: halogen, hydroxyl, methyl, ethyl, n-propyl, isopropyl, methoxyl, ethoxyl, ethoxycarbonyl, carboxyl, nitro, amino, and carbonyl.

In another preferred embodiment, the compound of Formula I according to the first aspect of the invention, is selected from a group consisting of compounds represented by the following structures:

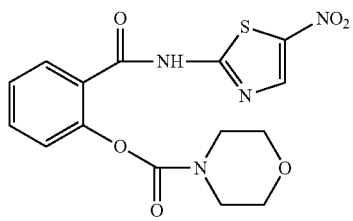

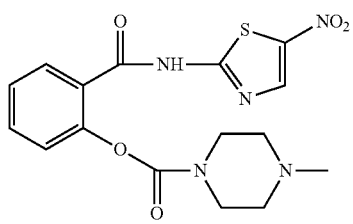

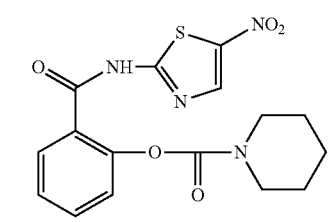

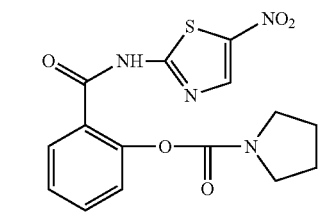

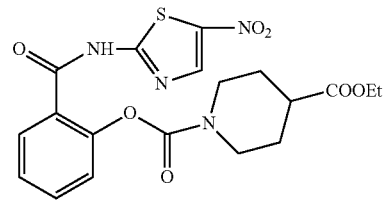

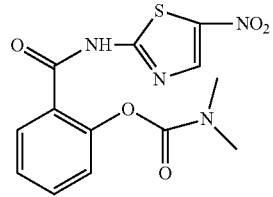

or a pharmaceutically acceptable salt, a hydrate or a solvate thereof.

In a second aspect, the invention relates to a pharmaceutical composition, comprising the compound of Formula I according to the first aspect of the invention, or a pharmaceutically acceptable salt, a hydrate or a solvate thereof.

In a preferred embodiment, the pharmaceutical composition according to the second aspect of the invention, further comprises a pharmaceutically acceptable carrier or excipient. The pharmaceutical composition can be prepared into a solid preparation, an injection, an external preparation, a spray, a liquid preparation or a compound preparation as desired.

In a third aspect, the invention relates to a method for preparing the compound of Formula I according to the first aspect of the invention, comprising in an aprotic solvent (such as dichloromethane, tetrahydrofuran (THF), and acetonitrile), reacting the compound represented by Formula II with triphosgene or diphosgene in an ice bath, to produce carbamyl chloride represented by Formula III, and without separation of the carbamyl chloride, adding tizoxanide to react the carbamyl chloride represented by Formula III with the phenolic hydroxyl of tizoxanide so as to produce the compound represented by Formula I,

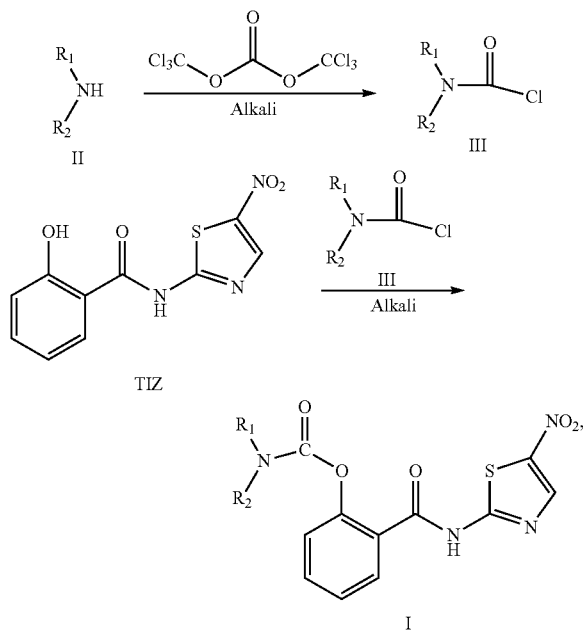

wherein, $R_1$ and $R_2$ are as defined in the first aspect of the invention.

In a fourth aspect, the invention relates to use of the compound of Formula I according to the first aspect of the invention or a pharmaceutically acceptable salt, hydrate or solvate thereof, or the pharmaceutical composition according to the second aspect of the invention, in the preparation of a medicament for treating and/or preventing an infection by parasite (including protozoan, helminth, etc.), hepatitis B (HBV), hepatitis C (HCV), influenza, a viral infectious disease caused by Rotavirus or Norovirus (e.g., viral enterogastritis caused by Rotavirus or Norovirus), or an infection caused by a bacterium such as *Clostridium difficile* or *Tubercle bacillus* (including drug-resistant *Tubercle bacillus*) or *Helicobacter pylori*, or in the preparation of a medicament for inhibiting biofilm formation caused by a bacterium.

The parasite of the invention includes: *Giardia, Amoeba, Cryptosporidium, Cyclospora, Trichomonad, Encephalitozoon intestinalis, Isospora belli, Blastocystis hominis, Balantidium coli, Ascarislumbricoides, Enterocytozoon bieneusi, Tapeworm* (including *Taenia saginata, Hymenolepis nana*), *Diplacanthus nanus, Giardia lamblia, Leishmania, Fasciola hepatica*, etc.

In the fifth aspect, the invention relates to a method for treating and/or preventing a disease in a mammal in need thereof, comprising administering to the mammal in need thereof a therapeutically or prophylactically effective amount of the compound of Formula I according to the first aspect of the invention or a pharmaceutically acceptable salt, hydrate or solvate thereof, or the pharmaceutical composition according to the second aspect of the invention, wherein the disease includes an infection by a parasite (including protozoan, helminth, etc.), hepatitis B (HBV), hepatitis C (HCV), influenza, a viral infectious disease caused by Rotavirus or Norovirus (e.g., viral enterogastritis caused by Rotavirus or Norovirus), or an infection caused by a bacterium such as *Clostridium difficile* or *Tubercle bacillus* (including drug-resistant *Tubercle bacillus*) or *Helicobacter pylori*.

In the sixth aspect, the invention relates to a method for inhibiting biofilm formation caused by a bacterium in a mammal in need thereof, comprising administering to the mammal in need thereof a therapeutically or prophylactically effective amount of the compound of Formula I according to the first aspect of the invention or a pharmaceutically acceptable salt, hydrate or solvate thereof; or the pharmaceutical composition according to the second aspect of the invention.

The term "alkyl" used herein refers to a saturated, linear or branched monovalent hydrocarbyl, having 1-12 carbon atoms, preferably 1-4 or 1-3 carbon atoms. Typical examples of "alkyl" include, but are not limited to methyl, ethyl, n-propyl, isopropyl, n-butyl, isobutyl, tert-butyl, n-pentyl, tert-amyl, neo-pentyl, hexyl, heptyl, octyl, etc.

The term "amino" used herein refers to —$NH_2$.
The term "hydroxyl" used herein refers to —OH.
The term "carbonyl" used herein refers to —C=O.
The term "carboxyl" used herein refers to —C(O)OH.
The term "nitro" used herein refers to —$NO_2$.
The term "alkoxycarbonyl" used herein refers to —C(O)OR', wherein R' is selected from the alkyl defined herein. Typical examples of "alkoxycarbonyl" include, but are not limited to —C(O)OCH$_3$, —C(O)OC$_2$H$_5$, etc.

The term "alkoxyl" used herein refers to —OR', wherein R' is selected from the alkyl defined herein. Typical examples of "alkoxyl" include, but are not limited to methoxyl, ethoxyl, n-propoxy, isopropoxy, n-butoxy, tert-butoxy, sec-butoxy, etc.

The term "heterocycle" used herein refers to cycloalkyl comprising one, two or more heteroatoms independently selected from N, O and S. Typical examples of "heterocycle" include, but are not limited to piperazinyl, morpholinyl, piperidyl, tetrahydrofuryl, pyrrolidinyl, furyl, imidazolyl, pyridyl, etc.

The term "halogen" used herein refers to F, Cl, Br or I. The preferred halogen is F, Cl or Br.

The groups defined by the above-mentioned terms may be optionally mono- or multi-substituted with —CN, —OH, —$NH_2$, $C_{1-4}$ alkyl, $C_{1-4}$ alkylamino, $C_{1-4}$ alkoxyl or halogen.

When the name of a compound used herein is not consistent with the chemical structural formula, the chemical structural formula will prevail.

BENEFICIAL EFFECTS OF THE INVENTION

The invention provides tizoxanide carbamate compounds of Formula I, which can be converted into the form of tizoxanide in vivo so as to exert an action against protozoans, helminths, viruses or bacteria. In addition, for the compounds of Formula I calculated as nitazoxanide, the bioavailability and the blood concentration are improved significantly, the effective blood concentration is retained for a longer time, and the blood concentration curve is more stable.

DESCRIPTION OF THE DRAWINGS

FIG. 1: The concentration-time curves of tizoxanide in plasma after oral administration of nitazoxanide and Compound 1, 2, 3, 4, 5, 6 in mice, respectively.

SPECIFIC MODES FOR CARRYING OUT THE INVENTION

The embodiments of the invention are described by combining the following examples. However, a person skilled in the art understands that the following examples are only intended to describe the invention, and shall not be regarded as defining the scope of the invention. When the particular techniques or conditions are not indicated in Examples, the invention is carried out according to the techniques or conditions described in the prior art documents or according to the product instruction. The reagents or apparatuses, the manufacturers of which are not indicated, are the conventional products that are commercially available.

EXAMPLE 1

Preparation of 2-(5-nitrothiazol-2-yl-carbamoyl) phenylmorpholine-4-carboxylate (Compound 1)

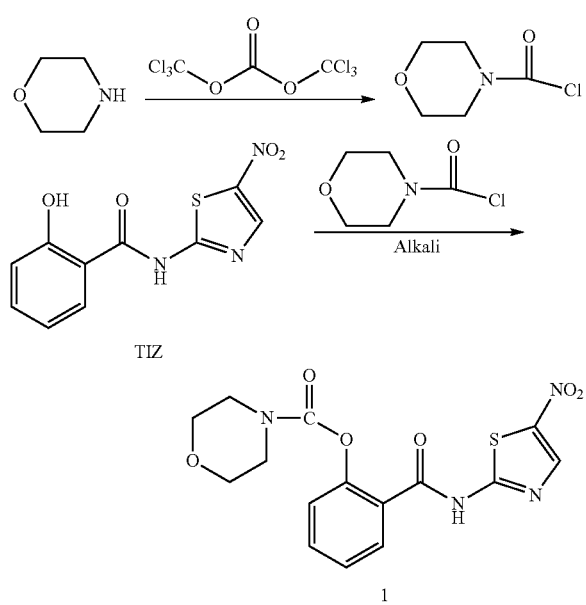

In an ice bath, to a reaction bottle, a solution of solid triphosgene (594 mg, 1.85 mmol) in dichloroethane (20 mL) was added, and a solution of morpholine (0.436 g, 5.0 mmol) dissolved in pyridine (8 mL) was added slowly dropwise. The reaction was carried out in the ice bath for 4-5 h. $N_2$ gas was introduced to remove the excessive triphosgene, the ice bath was removed, a solution of tizoxanide (1.325 g, 5.0 mmol) in THF (10 mL) was added at room temperature, and the reaction was carried out under stirring overnight. The product was extracted with ethyl acetate, the ethyl acetate phase was washed sequentially with water and saturated salt solution, the organic phase was dried with anhydrous sodium sulphate, the solvent was removed by distillation under reduced pressure, and the resultant residue was subjected to silica gel column chromatography, to obtain the product 1.23 g, with a yield of 65.08%, $^1$H-NMR (CDCl$_3$, 400 Hz) δppm: 10.66 (s, 1H), 8.19 (s, 1H), 7.93 (dd, J=1.56, 7.93 Hz, 1H), 7.66-7.62 (m, 1H), 7.42-7.39 (m, 1H), 7.25-7.26 (m, 1H), 3.76-3.81 (m, 6H), 3.60-3.61 (m, 2H). ESI-MS m/z: 379.3[MH]$^+$, 401.3[MNa]$^+$.

EXAMPLE 2

Preparation of 2-(5-nitrothiazol-2-yl-carbamoyl) phenyl-4-methylpiperazine-1-carboxylate (Compound 2)

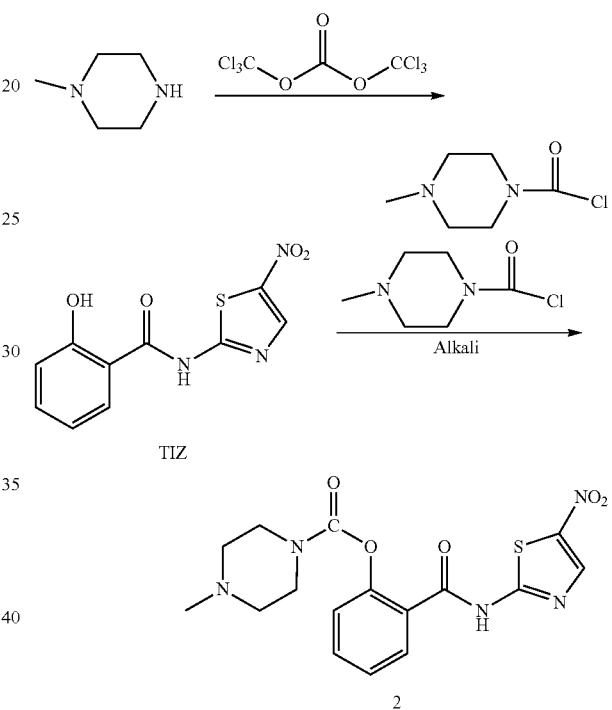

In an ice bath, to a reaction bottle, a solution of solid triphosgene (594 mg, 1.85 mmol) in dichloroethane (20 mL) was added, and a solution of 1-methyl piperidine (0.501 g, 5.0 mmol) dissolved in pyridine (8 mL) was added slowly dropwise. The reaction was carried out in the ice bath for 4-5 h. $N_2$ gas was introduced to remove the excessive triphosgene, the ice bath was removed, and a solution of tizoxanide (1.325 g, 5.0 mmol) in THF (10 mL) was added at room temperature. The reaction was carried out under stirring overnight. The product was extracted with ethyl acetate, the ethyl acetate phase was washed sequentially with water and saturated salt solution, the organic phase was dried with anhydrous sodium sulphate, the solvent was removed by distillation under reduced pressure, and the resultant residue was subjected to silica gel column chromatography, to obtain the product 0.96 g, with a yield of 48.98%. $^1$H-NMR (CDCl$_3$, 400 Hz) δppm: 8.25 (s, 1H) 7.92 (dd, J=1.68, 7.84 Hz, 1H), 7.65-7.60 (m, 1H), 7.41-7.37 (m, 1H), 7.24 (d, J=8.12 Hz, 2H), 3.83 (brs, 2H), 3.65 (brs, 2H), 2.62 (brs, 2H), 2.53 (brs, 2H), 2.41 (s, 3H). ESI-MS m/z: 392 [MH]$^+$, 414 [MNa]$^+$.

EXAMPLE 3

Preparation of 2-((5-nitrothiazol-2-yl)carbamoyl) phenyl-piperidine-4-carboxylate (Compound 3)

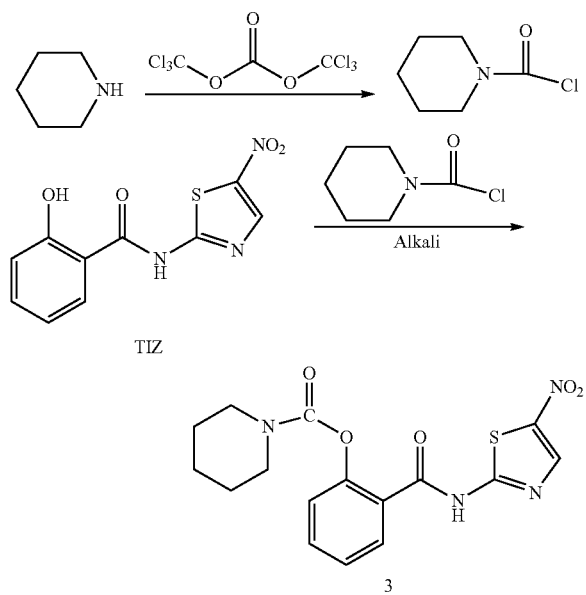

In an ice bath, to a reaction bottle, a solution of solid triphosgene (594 mg, 1.85 mmol) in dichloroethane (20 mL) was added, and a solution of piperidine (0.43 g, 5.0 mmol) dissolved in pyridine (8 mL) was added slowly dropwise. The reaction was carried out in the ice bath for 4-5 h. $N_2$ gas was introduced to remove the excessive triphosgene, the ice bath was removed, and a solution of tizoxanide (1.325 g, 5.0 mmol) in THF (10 mL) was added at room temperature. The reaction was carried out under stirring overnight. The product was extracted with ethyl acetate, the ethyl acetate phase was washed sequentially with water and saturated salt solution, the organic phase was dried with anhydrous sodium sulphate, the solvent was removed by distillation under reduced pressure, and the resultant residue was subjected to silica gel column chromatography, to obtain the product 1.26 g, with a yield of 67.02%, $^1$H-NMR (CDCl$_3$, 400 Hz) δppm: 8.28 (s, 1H), 7.97 (dd, J=1.68, 7.84 Hz, 1H), 7.64-7.60 (m, 1H), 7.41-7.37 (m, 1H), 7.26-7.22 (m, 1H), 3.72 (br s, 2H), 3.55 (br s, 2H), 1.65 (br s, 6H). ESI-MS m/z: 377 [MH]$^+$, 399 [MNa]$^+$.

EXAMPLE 4

Preparation of 2-((5-nitrothiazol-2-yl)carbamoyl) phenyl-pyrrolidine-1-carboxylate (Compound 4)

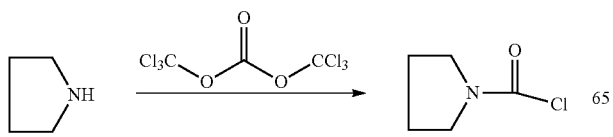

In an ice bath, to a reaction bottle, a solution of solid triphosgene (594 mg, 1.8 mmol) in dichloroethane (20 mL) was added, and a solution of pyrrole (0.345 g, 5.0 mmol) dissolved in pyridine (8 mL) was added slowly dropwise. The reaction was carried out in the ice bath for 4-5 h. $N_2$ gas was introduced to remove the excessive triphosgene, the ice bath was removed, and a solution of tizoxanide (1.325 g, 5.0 mmol) in THF (10 mL) was added at room temperature. The reaction was carried out under stirring overnight. The product was extracted with ethyl acetate, the ethyl acetate phase was washed sequentially with water and saturated salt solution, the organic phase was dried with anhydrous sodium sulphate, the solvent was removed by distillation under reduced pressure, and the resultant residue was subjected to silica gel column chromatography, to obtain the product 1.24 g, with a yield of 68.51%, $^1$H-NMR(CDCl$_3$, 400 Hz) δppm: 11.08 (s, 1H), 8.22 (s, 1H), 8.00 (dd, J=1.82, 7.70 Hz, 1H), 7.65-7.60 (m, 1H), 7.40-7.31 (m, 2H), 3.73 (t, J=6.72 Hz, 2H), 3.52 (t, J=6.72 Hz, 2H), 2.06-1.96 (m, 4H). ESI-MS m/z: 363[MH]$^+$, 385[MNa]$^+$.

EXAMPLE 5

Preparation of 2-(5-nitrothiazol-2-yl-carbamoyl) phenyl-4-(2-ethoxy-2-oxoethyl) piperidine-1-carboxylate (Compound 5)

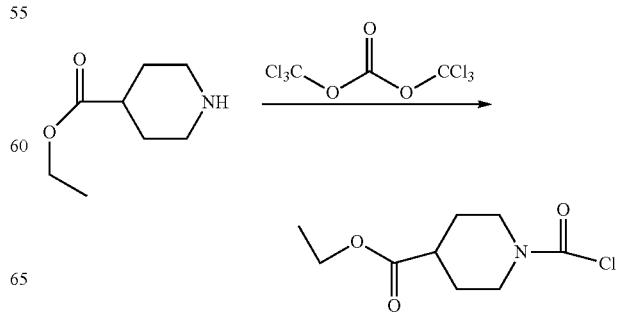

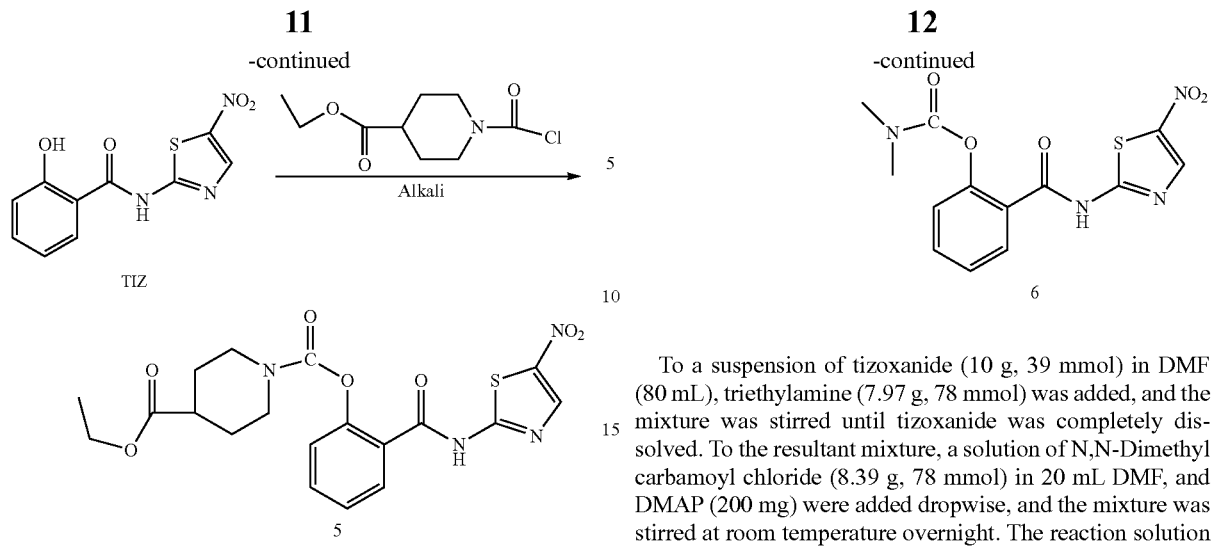

In an ice bath, to a reaction bottle, a solution of triphosgene (594 mg, 2 mmol) in dichloroethane (10 mL), ethyl piperidine-4-carboxylate (786 mg, 500 mmol), and a solution of triethylamine (0.7 mL) in dichloroethane (5 mL) were added sequentially. After stirring at room temperature for 2 h, the reaction mixture was distilled under reduced pressure, and the resultant residue was dissolved in anhydrous THF (10 mL), and in an ice bath again, a solution of tizoxanide (1.325 g) in THF (10 mL), triethylamine (549 mg, 5.0 mmol), and 4-dimethylaminopyridine (DMAP) 100 mg were added. The mixture was stirred at room temperature overnight, and distilled water was then added to the reaction mixture. The resultant mixture was extracted with ethyl acetate, the ethyl acetate phase was washed sequentially with water and saturated salt solution, the organic phase was dried with anhydrous sodium sulphate, the solvent was removed by distillation under reduced pressure, and the resultant residue was subjected to silica gel column chromatography, to obtain the product 0.73 g, with a yield of 55.09%, $^1$H-NMR (DMSO-d6,400 Hz) δppm: 13.57 (s, 1H), 8.68 (s, 1H), 7.77 (d, J=7.6 Hz, 1H), 7.67-7.63 (m, 1H), 7.43-7.39 (m, 1H), 7.31-7.33 (m, 1H), 4.06-4.11 (m, 3H), 3.81-3.84 (m, 1H), 3.10-3.17 (m, 1H), 2.87-2.93 (m, 1H), 1.66-1.88 (m, 3H), 1.36-1.39 (m, 1H), 1.19 (t, J=7.2 Hz, 3H). ESI-MS: m/z: 449.1[MH]$^+$, 471.1[MNa]$^+$.

EXAMPLE 6

Preparation of 2-(5-nitrothiazol-2-yl-carbamoyl) phenyl-4-(2-ethoxy-2-oxoethyl) piperidine-1-carboxylate (Compound 6)

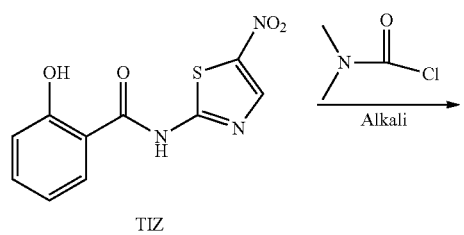

To a suspension of tizoxanide (10 g, 39 mmol) in DMF (80 mL), triethylamine (7.97 g, 78 mmol) was added, and the mixture was stirred until tizoxanide was completely dissolved. To the resultant mixture, a solution of N,N-Dimethyl carbamoyl chloride (8.39 g, 78 mmol) in 20 mL DMF, and DMAP (200 mg) were added dropwise, and the mixture was stirred at room temperature overnight. The reaction solution was poured into 300 mL ice-water containing 7.5 mL concentrated hydrochloric acid. The insoluble substance was removed by filtration. The filtrate was extracted with dichloromethane 3 times, the dichloromethane phase was washed sequentially with water and saturated salt solution, and was dried with anhydrous sodium sulphate, the solvent was removed by distillation under reduced pressure, and the resultant residue was subjected to silica gel column chromatography, to obtain the product 6 g, with a yield of 45%. $^1$H-NMR (DMSO-d6, 400 Hz) δppm: 13.53 (s, 1H), 8.70 (s, 1H), 7.76 (d, J=7.6 Hz, 1H), 7.62-7.67 (m, 1H), 7.37-7.41 (m, 1H), 7.31-7.33 (m, 1H), 3.03 (s, 3H), 2.83 (m, ESI-MS: m/z: 337.1[MH]$^+$.

EXAMPLE 7

Pharmacokinetic Evaluation and Result of Oral Administration of the Compounds in Mice ICR mice (SPS grade, male, 25±2 mg), were grouped randomly depending on body weight, 3 mice for each group. The subject compound nitazoxanide and Compound 1, 2, 3, 4, 5, 6 (Sample preparation: 0.03257 mmol of the subject compound was dissolved in 100 uL DMSO, with the addition of 10 mL 0.5% CMC-Na solution, to prepare a sample at 3.257 μmol/mL, and the sample was intragastrically administered at a dose of 10 mL/kg (equivalent to a dose of 32.57 μmol/kg tizoxanide) to each mice) were intragastically administered at a dose equivalent to 32.57 μmol/kg tizoxanide, wherein nitazoxanide was used as positive control, and 0.1 ml blood was taken from veins of Fundus Oculi at 0.08, 0.25, 0.5, 1, 2, 4, 6, 8 and 12 h after administration, placed in a Heparin Sodium-containing centrifuge tube, and centrifuged at 3000 g for 20 min. The plasma was taken and stored in a −20° C. refrigerator for further detection.

During the detection, 50 μL plasma was taken, with the addition of an internal standard solution (5000 ng/ml, glipizide aqueous solution, 10 μL), and the addition of acetonitrile (200 μL), then mixed well. The mixture was vortexed for 3 min, and centrifuged for 10 min (at a relative centrifugal force (RCF) of 8500 g). The supernatant (50 μL) was mixed with water (50 μL), and 10 μL was drawn for LC/MS/MS analysis, so as to detect the blood concentration of tizoxanide. The results are shown in Table 1, Table 2 and FIG. 1.

TABLE 1

Blood concentrations (Mean ± SD, n = 3) of tizoxanide after oral administration of the compound nitazoxanide and Compound 1, 2, 3, 4, 5, 6 in mice, respectively

| time (h) | NTZ | Compound 1 | Compound 2 | Compound 3 | Compound 4 | Compound 5 | Compound 6 |
|---|---|---|---|---|---|---|---|
| 0.08 | 127.23 ± 22.46 | 120.62 ± 53.49 | 495.61 ± 161.89 | 139.51 ± 20.57 | 156.67 ± 34.92 | 329.85 ± 37.88 | 25.33 ± 8.09 |
| 0.25 | 329.39 ± 111.17 | 397.98 ± 72.65 | 444.34 ± 80.08 | 254.20 ± 67.14 | 411.33 ± 133.87 | 148.92 ± 24.08 | 128.02 ± 23.18 |
| 0.5 | 94.65 ± 24.48 | 535.69 ± 267.17 | 222.08 ± 93.37 | 787.61 ± 90.92 | 561.54 ± 129.43 | 92.03 ± 11.37 | 275.35 ± 81.27 |
| 1 | 19.69 ± 5.62 | 468.37 ± 235.43 | 233.28 ± 44.18 | 812.20 ± 199.523 | 705.78 ± 113.32 | 48.61 ± 8.32 | 430.11 ± 155.20 |
| 2 | 13.91 ± 3.60 | 154.82 ± 68.23 | 200.57 ± 78.52 | 541.76 ± 49.39 | 477.14 ± 127.03 | 13.39 ± 2.27 | 478.64 ± 103.31 |
| 4 | 8.22 ± 5.08 | 57.26 ± 34.49 | 79.88 ± 126.76 | 226.51 ± 92.02 | 204.24 ± 36.11 | 4.18 ± 1.51 | 266.56 ± 31.28 |
| 6 | 3.46 ± 1.66 | 52.25 ± 53.09 | 5.83 ± 5.45 | 135.86 ± 18.47 | 45.94 ± 30.08 | 6.14 ± 4.10 | 131.48 ± 24.35 |
| 8 | 0.61 ± 0.12 | 21.74 ± 5.95 | 3.87 ± 4.45 | 44.67 ± 4.88 | 33.29 ± 47.42 | 2.90 ± 1.04 | 104.15 ± 95.20 |
| 12 | 4.90 ± 6.45 | 4.74 ± 0.33 | 16.07* | 39.80 ± 49.88 | 17.95 ± 28.44 | 0.51 ± 0.04 | 32.50 ± 17.65 |

Note:
ND: lower than limit of quantitation:
*a group of measured values, no SD value

TABLE 2

Pharmacokinetic parameters (Mean ± SD, n = 3) calculated as tizoxanide, after oral administration of nitazoxanide and Compound 1, 2, 3, 4, 5, 6 in mice

| Parameters | Unit | NTZ | 1 | 2 | 3 | 4 | 5 | 6 |
|---|---|---|---|---|---|---|---|---|
| $T_{max}$ | h | 0.25 ± 0.00 | 0.58 ± 0.38 | 0.14 ± 0.10 | 0.83 ± 0.29 | 1.00 ± 0.00 | 0.08 ± 0.00 | 1.70 ± 0.55 |
| $C_{max}$ | ng/mL | 329.4 ± 111.2 | 681.2 ± 194.5 | 506.5 ± 144.6 | 875.2 ± 90.8 | 705.8 ± 113.3 | 329.8 ± 37.9 | 430.11 ± 155.20 |
| Ke | 1/h | 0.41 ± 0.23 | 0.36 ± 0.08 | 0.58 ± 0.16 | 0.35 ± 0.10 | 0.48 ± 0.21 | 0.37 ± 0.11 | 0.32 ± 0.05 |
| $t_{1/2}$ | h | 2.02 ± 0.92 | 2.01 ± 0.45 | 1.27 ± 0.38 | 2.13 ± 0.73 | 1.76 ± 1.06 | 1.95 ± 0.11 | 2.34 ± 0.37 |
| $AUC_{0-t}$ | h*ng/mL | 185.8 ± 18.3 | 1176.8 ± 354.8 | 902.3 ± 381.3 | 2726.3 ± 386.5 | 2197.7 ± 263.8 | 193.9 ± 14.7 | 2160.7 ± 766.6 |
| $AUC_{0-\infty}$ | h*ng/mL | 198.5 ± 28.5 | 1190.5 ± 353.0 | 920.4 ± 388.8 | 2883.7 ± 611.2 | 2272.2 ± 359.6 | 195.3 ± 15.1 | 2345.5 ± 643.4 |
| $MRT_{0-t}$ | h | 1.46 ± 0.81 | 2.22 ± 0.30 | 1.78 ± 0.51 | 2.85 ± 0.37 | 2.47 ± 0.76 | 1.52 ± 0.17 | 3.22 ± 0.55 |
| $MRT_{0-\infty}$ | h | 2.15 ± 1.66 | 2.38 ± 0.24 | 1.98 ± 0.59 | 3.44 ± 1.17 | 2.84 ± 1.37 | 1.62 ± 0.15 | 3.85 ± 0.49 |
| $F_{(rt)}$ | % | — | 633.29 ± 190.95 | 485.59 ± 205.18 | 1467.20 ± 208.01 | 1182.73 ± 141.94 | 104.35 ± 7.93 | 1162.92 ± 418.90 |

The pharmacokinetic screening results after oral administration in mice show:

(1) Compound 1, Compound 3, Compound 4 and Compound 6 were much better than the control agent nitazoxanide (NTZ) with respect to oral absorption; said four Compounds (calculated as tizoxanide) had a $C_{max}$ 2-fold, 2.7-fold, 2.14-fold and 1.31-fold higher than that of nitazoxanide, respectively; had a $T_{max}$ of 0.58 h, 0.83 h, 1.00 h and 1.7 h, respectively (which were obviously delayed compared to nitazoxanide with a time to peak ($T_{max}$) of 0.25 h); had a Mean Retention Time (MRT) of 2.38 h, 3.44 h, 2.84 h and 3.22 h calculated as tizoxanide, respectively (which were obviously delayed compared to nitazoxanide with a MRT of 2.15 h); had an Area Under concentration-time Curve (AUC) of 1190.5 h*ng/mL, 2883.7 h*ng/mL, 2272.2 h*ng/mL, and 2160.7*ng/mL calculated astizoxanide, respectively (which were greatly increased compared to 198.5 h*ng/mL of nitazoxanide), and were 6.3-fold, 14.7-fold, 11.8-fold and 11.62-fold of that of nitazoxanide (i.e., their relative bioavailability calculated as tizoxanide was 6.3-fold, 14.7-fold, 11.8-fold and 11.62-fold of that of nitazoxanide, respectively).

(2) Compound 2 was faster than the control agent nitazoxanide (NTZ) with respect to oral absorption, and had a $T_{max}$ of 0.14 h, which was smaller than 0.25 h of nitazoxanide; Compound 2 had a $C_{max}$ 1.5-fold of that of nitazoxanide calculated as tizoxanide; Compound 5 was comparable to nitazoxanide with respect to $C_{max}$ value calculated as tizoxanide; after oral administration of Compound 2, Compound 2 had an AUC of 920.4 h*ng/mL calculated as tizoxanide, which was greatly increased compared to 198.5 h*ng/mL of nitazoxanide, and was 4.9-fold of that of nitazoxanide (i.e., the relative bioavailability calculated as tizoxanide was 4.9 fold of that of nitazoxanide).

(3) Compound 5 was faster than the control agent nitazoxanide (NTZ) with respect to oral absorption, but was comparable to nitazoxanide with respect to parameters such as $T_{max}$, $C_{max}$, MRT and AUC calculated astizoxanide.

Conclusion: Compound 1, 2, 3, 4, 6, were significantly superior to the control agent nitazoxanide (NTZ) with respect to parameters such as $C_{max}$, Mean Retention Time (MRT), Area Under concentration-time Curve (AUC) and relative bioavailability ($F_{rt}$) calculated as tizoxanide. Compound 5 was faster than the control agent nitazoxanide (NTZ) with respect to oral absorption, but was comparable to nitazoxanide with respect to parameters such as $T_{max}$, $C_{max}$, MRT and AUC calculated as tizoxanide.

Although the embodiments of the invention have been described in detail, a person skilled in the art would understand that a variety of modifications and replacements may be performed to the details according to all the teachings disclosed therein. These changes all fall into the protection scope of the invention. The scope of the invention is defined by the claims and any equivalent thereof.

The invention claimed is:

1. A compound selected from the following structures:

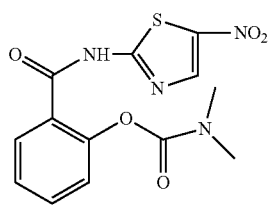

or a pharmaceutically acceptable salt, a hydrate or a solvate thereof.

2. A pharmaceutical composition, comprising the compound according to claim 1, a pharmaceutically acceptable salt, a hydrate or a solvate thereof.

3. The pharmaceutical composition according to claim 2, further comprising a pharmaceutically acceptable carrier or excipient.

4. The pharmaceutical composition according to claim 3, said pharmaceutical composition is in the form of a solid preparation, an injection, an external preparation, a spray, a liquid preparation or a compound preparation.

5. A method for treating a disease in a mammal in need thereof, comprising administering to the mammal in need thereof a therapeutically effective amount of the compound according to claim 1, or a pharmaceutically acceptable salt, hydrate or solvate thereof, wherein the disease is selected from an infection by a parasite, hepatitis B, hepatitis C, influenza, a viral infectious disease caused by Rotavirus or Norovirus, and an infection caused by a bacterium.

6. A method for inhibiting biofilm formation caused by a bacterium in a mammal in need thereof, comprising administering to the mammal in need thereof a therapeutically effective amount of the compound according to claim 1 or a pharmaceutically acceptable salt, hydrate or solvate thereof.

7. The method according to claim 5, wherein parasite is protozoan, or helminth.

8. The method according to claim 5, wherein said viral infection disease caused by Rotavirus or Norovirus is viral enterogastritis caused by Rotavirus or Norovirus.

9. The method according to claim 5, wherein said infection caused by a bacterium is an infection caused by *Clostridium difficile* or *Tubercle bacillus* or *Helicobacter pylori*.

10. The method according to claim 8, wherein said *Tubercle bacillus* is drug-resistant *Tubercle bacillus*.

11. The method according to claim 5, wherein said parasite is selected from the group consisting of: *Giardia, Amoeba, Cryptosporidium, Cyclospora, Trichomonad, Encephalitozoon intestinalis, Isospora belli, Blastocystis hominis, Balantidium coli, Ascarislumbricoides, Enterocytozoon bieneusi, Tapeworm, Diplacanthus nanus, Giardia lamblia, Leishmania*, and *Fasciola hepatica*.

12. The method according to claim 11, wherein said parasite is *Tapeworm* and said *Tapeworm* is *Taenia saginata*, or *Hymenolepis nana*.

* * * * *